(12) United States Patent
Taylor et al.

(10) Patent No.: US 7,592,300 B2
(45) Date of Patent: ***Sep. 22, 2009

(54) ANTIMICROBIAL COMPOSITIONS CONTAINING AN AROMATIC CARBOXYLIC ACID AND A HYDRIC SOLVENT

(75) Inventors: Timothy J. Taylor, Phoenix, AZ (US); Earl P. Seitz, Jr., Scottsdale, AZ (US); Priscilla S. Fox, Phoenix, AZ (US); Janice Fuls, Fountain Hills, AZ (US)

(73) Assignee: The Dial Corporation, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/720,862

(22) Filed: Nov. 24, 2003

(65) Prior Publication Data
US 2005/0113276 A1    May 26, 2005

(51) Int. Cl.
*A61K 7/00*    (2006.01)
(52) U.S. Cl. .................. 510/130; 510/138; 510/157; 510/158
(58) Field of Classification Search ................ None
See application file for complete search history.

(56) References Cited

U.S. PATENT DOCUMENTS

| | | |
|---|---|---|
| 3,160,555 A | 12/1964 | Hamill et al. |
| 5,824,666 A | 10/1998 | Deckner et al. |
| 5,968,539 A | 10/1999 | Beerse et al. |
| 6,106,851 A | 8/2000 | Beerse et al. |
| 6,183,757 B1 | 2/2001 | Beerse et al. |
| 6,190,674 B1 | 2/2001 | Beerse et al. |
| 6,190,675 B1 | 2/2001 | Beerse et al. |
| 6,197,315 B1 | 3/2001 | Beerse et al. |
| 6,214,363 B1 | 4/2001 | Beerse et al. |
| 6,287,577 B1 | 9/2001 | Beerse et al. |
| 6,294,186 B1 * | 9/2001 | Beerse et al. ............... 424/405 |
| 6,861,397 B2 * | 3/2005 | Seitz et al. .................. 510/119 |
| 2002/0098159 A1 * | 7/2002 | Wei et al. ................... 424/70.1 |
| 2002/0168422 A1 * | 11/2002 | Hei et al. .................... 424/661 |

FOREIGN PATENT DOCUMENTS

| | | |
|---|---|---|
| WO | WO 98/55097 | 12/1998 |
| WO | WO 01/28338 | 4/2001 |
| WO | WO 2004/103321 | 12/2004 |

OTHER PUBLICATIONS

Anonymous: "Desinfection—B. Antiseptiques—Desinfectants" Internet Article XP002323518.

* cited by examiner

*Primary Examiner*—Necholus Ogden, Jr.
(74) *Attorney, Agent, or Firm*—Marshall, Gerstein & Borun LLP

(57) ABSTRACT

Antimicrobial compositions having an excellent antibacterial and antiviral effectiveness are disclosed. The antimicrobial compositions contain an aromatic carboxylic acid, a hydric solvent, a pH-adjusting compound, and water.

21 Claims, No Drawings

ANTIMICROBIAL COMPOSITIONS CONTAINING AN AROMATIC CARBOXYLIC ACID AND A HYDRIC SOLVENT

FIELD OF THE INVENTION

The present invention is directed to antimicrobial compositions, such as personal care compositions, having excellent antimicrobial effectiveness. More particularly, the present invention is directed to antimicrobial compositions comprising an aromatic carboxylic acid and a hydric solvent, which provides a substantial reduction, e.g., greater than 99%, in Gram positive and Gram negative bacterial populations and in viral populations, within one minute.

BACKGROUND OF THE INVENTION

Antimicrobial personal care compositions are known in the art. Especially useful are antimicrobial cleansing compositions, which typically are used to cleanse the skin and to destroy bacteria, viruses, and other microorganisms present on the skin, especially the hands, arms, and face of the user.

Another class of antimicrobial personal care compositions is the hand sanitizers. This class of compositions is used primarily by medical personnel to disinfect the hands and fingers. A hand sanitizer is applied to, and rubbed into, the hands and fingers, and the composition is allowed to evaporate from the skin. Wiping of the composition from the skin often is not necessary because the high alcohol content of some hand sanitizers leads to a fast and essentially complete evaporation of the composition from the skin.

Antimicrobial compositions are used, for example, in the health care industry, food service industry, meat processing industry, and in the private sector by individual consumers. The widespread use of antimicrobial compositions indicates the importance consumers place on controlling bacteria and other microorganism populations on skin. It is important, however, that antimicrobial compositions provide a substantial and broad spectrum reduction in microorganism populations quickly and without problems associated with toxicity and skin irritation.

Antimicrobial cleansing compositions typically contain an active antimicrobial agent, a surfactant, and various other ingredients, for examples, dyes, fragrances, thickeners, skin conditioners, and the like, in an aqueous carrier. Several different classes of antimicrobial agents have been used in antimicrobial cleansing compositions. Examples of antibacterial agents include a bisguanidine (e.g., chlorhexidine digluconate), diphenyl compounds, benzyl alcohols, trihalocarbanilides, quaternary ammonium compounds, ethoxylated phenols, and phenolic compounds, such as halosubstituted phenolic compounds, like PCMX (i.e., p-chloro-m-xylenol) and triclosan (i.e., 2,4,4'-tri-chloro-2'-hydroxy-diphenyl ether). Present-day antimicrobial compositions based on such antimicrobial agents exhibit a wide range of antimicrobial activity, ranging from low to high, depending on the microorganism to be controlled and the particular antimicrobial composition.

Hand sanitizers contain a high percentage of an alcohol, such as ethanol. When a high percent of alcohol present in a hand sanitizer, the alcohol itself acts as a disinfectant. In addition, the alcohol quickly evaporates to obviate wiping or rinsing skin treated with the hand sanitizer. Hand sanitizers containing a high percentage of an alcohol, i.e., about 40% or greater by weight of the composition, however, have a tendency to dry and irritate the skin.

Commercial antimicrobial compositions generally provide a low to moderate antimicrobial activity. Antimicrobial activity is assessed against a broad spectrum of microorganisms, including viruses and Gram positive and Gram negative bacteria. The log reduction, or alternatively the percent reduction, in bacterial and viral populations provided by the antimicrobial composition correlates to antimicrobial activity. A log reduction of 3-5 is most preferred, a 1-3 reduction is preferred, whereas a log reduction of less than 1 is least preferred, for a particular contact time, generally ranging from 15 seconds to 5 minutes. Thus, a highly preferred antimicrobial composition exhibits a 3-5 log reduction against a broad spectrum of microorganisms in a short contact time. Prior disclosures illustrate attempts to provide such antimicrobial compositions, which, to date, do not provide the rapid, broad range control of microorganisms desired by consumers.

The use of organic carboxylic acids in antimicrobial compositions is known. One often used aromatic carboxylic acid is salicylic acid. Various investigators have reported improvements in antimicrobial compositions, especially in personal care compositions, that incorporate salicylic acid. For example, Deckner et al. U.S. Pat. No. 5,824,666 discloses oil-in-water emulsions containing salicylic acid as an anti-acne agent, and a surfactant, for use as leave-on moisturizing products.

Beerse et al. U.S. Pat. No. 5,968,539 discloses a rinse-off antimicrobial agent containing an antimicrobial agent (e.g., triclosan), a proton donating agent (e.g., salicylic acid), and an anionic surfactant. Other patents that disclose the use of salicylic acid in admixture with an antimicrobial agent include Beerse et al. U.S. Pat. Nos. 6,106,851; 6,183,757; 6,190,674; 6,190,675; 6,197,315; 6,214,363; and 6,287,577. Although these patents disclose the use of salicylic acid in antimicrobial compositions, each disclosure relied upon either (1) an antimicrobial active, such as triclosan, in the composition, or (2) a composition pH of 3.5 or less. Each of the above patents also disclose including a surfactant in the composition.

Prior disclosures have not addressed the use of salicylic acid, or other aromatic carboxylic acids, as the primary, or sole, antibacterial agent present in the antimicrobial composition, especially at a pH of about 3.5 or greater, e.g., about 3.5 to about 5. The prior disclosures also did not address the use of an antimicrobial composition containing an aromatic carboxylic acid as the primary, or sole, antimicrobial agent, and that is free, or at least essentially free, of a surfactant.

Accordingly, a need exists for antimicrobial compositions that are highly efficacious against a broad spectrum of Gram positive and Gram negative bacteria, and viruses, in a short time period, and wherein the antimicrobial activity is attributed primarily, or solely, to the presence of an aromatic carboxylic acid and a hydric solvent in the composition. The present invention is directed to such antimicrobial compositions.

SUMMARY OF THE INVENTION

The present invention relates to antimicrobial compositions for topical use on surfaces, including animate and inanimate surfaces. The compositions of the present invention are particularly useful as antimicrobial compositions for use in personal care applications.

The present invention particularly relates to antimicrobial compositions that provide a substantial reduction in Gram positive and Gram negative bacteria, and viruses, in less than about one minute. More particularly, the present invention relates to antimicrobial compositions containing an aromatic carboxylic agent, a hydric solvent, and water, and that is free, or at least essentially free, of a surfactant.

Accordingly, one aspect of the present invention is to provide an antimicrobial composition comprising: (a) about 0.1% to about 10%, by weight, of an aromatic carboxylic acid; (b) about 5% to about 50%, by weight, of a hydric solvent; (c) a sufficient amount of a pH-adjusting compound to provide a composition having a pH of about 2 to about 5.5, and (d) water. The antimicrobial composition also is free, or essentially free, of a surfactant i.e., includes 0% to about 0.2%, by weight, of a surfactant.

Another aspect of the present invention is to provide an antimicrobial composition containing an aromatic carboxylic acid, for example, benzoic acid or salicylic acid, wherein the aromatic carboxylic acid has a pKa of about 2.5 or greater, and preferably about 3 or greater.

Still another aspect of the present invention is to provide an antimicrobial composition containing a hydric solvent having a Hansen solubility parameter of about 38 or less, and preferably about 35 or less.

Another aspect of the present invention is to provide an antimicrobial composition utilizing an aromatic carboxylic acid and a hydric solvent as the primary, or sole, antimicrobial agents.

Yet another aspect of the present invention is to provide an antimicrobial composition that exhibits a log reduction against Gram positive bacteria (i.e., S. aureus) of at least 3 after 30 seconds of contact.

Still another aspect of the present invention is to provide an antimicrobial composition that exhibits a log reduction against Gram negative bacteria (i.e., E. coli) of at least 3 after 30 seconds of contact.

Another aspect of the present invention is to provide an antimicrobial composition that exhibits a substantial log reduction against Gram positive and Gram negative bacteria, and has a pH of about 2 to about 5.5.

Yet another aspect of the present invention is to provide an antimicrobial composition that exhibits a log reduction against viruses (e.g., rhinovirus and rotavirus) of at least 3 after 30 seconds of contact.

Another aspect of the present invention is to provide consumer products based on antimicrobial composition of the present invention, for example, a skin cleanser, a body splash, a surgical scrub, a wound care agent, a hand sanitizer, a disinfectant, a mouthwash, a pet shampoo, a hard surface sanitizer, and the like.

A further aspect of the present invention is to provide a method of reducing the Gram positive and/or Gram negative bacteria populations, and viral populations, on animal tissue, including human tissue, by contacting the tissue, like the dermis, with a composition of the present invention for a sufficient time, such as about 15 seconds to 5 minutes, to reduce the bacteria level to a desired level. The composition can be wiped or rinsed from the skin. In some embodiments, the composition is allowed to remain on the skin until the volatile components of the composition evaporate.

The above and other novel aspects and advantages of the present invention are illustrated in the following, nonlimiting detailed description of the preferred embodiments.

DETAILED DESCRIPTION OF THE PREFERRED EMBODIMENTS

Personal care products incorporating an active antimicrobial agent have been known for many years. Since the introduction of antimicrobial personal care products, many claims have been made that such products provide antimicrobial properties. However, to be most effective, an antimicrobial composition should provide a high log reduction against a broad spectrum of organisms in as short a contact time as possible. It also would be beneficial if the antimicrobial composition provided a residual benefit.

Present-day products especially lack efficacy against Gram negative bacteria, such as E. coli, which are of particular concern to human health. The present invention, therefore, is directed to antimicrobial compositions having an exceptionally high broad spectrum antimicrobial efficacy, as measured by a rapid kill of bacteria (i.e., time kill), which is to be distinguished from a persistent kill.

The present compositions are antimicrobial compositions having an excellent effectiveness against both Gram negative and Gram positive bacteria, and against viruses. The present composition also exhibits a rapid microbial kill. An antimicrobial composition of the present invention comprises: (a) about 0.1% to about 10%, by weight, of an aromatic carboxylic acid as an antimicrobial agent; (b) about 0.1% to about 40%, by weight, of a hydric solvent; (c) a sufficient amount of a pH-adjusting compound to provide a pH of about 2 to about 5.5; and (d) water. The composition is free, or essentially free, of a surfactant. The compositions exhibit a log reduction against Gram positive and Gram negative bacteria, and against viruses, of about 3 after 30 seconds contact. The compositions also are mild, and provide a persistent kill because it is not necessary to rinse or wipe the compositions from the skin.

In accordance with the present invention, the antimicrobial compositions comprise an active antimicrobial agent (i.e., an aromatic carboxylic acid), a hydric solvent, a pH-adjusting compound, and a carrier comprising water. The aromatic carboxylic acid is the sole, or primary, antimicrobial agent in the composition. The hydric solvent may provide some antimicrobial efficacy. The present compositions are free, or essentially free, of surfactants, i.e., contain 0% to about 0.2%, by weight, of compounds that exhibit surface activity. The compositions can further include a hydrotrope and additional optional ingredients disclosed hereafter, such as dyes, skin conditioners, vitamins, and perfumes.

The following illustrates nonlimiting embodiments of the present invention, and a discussion of various ingredients present in the antimicrobial compositions.

Antimicrobial Agent

An antimicrobial agent is present in a composition of the present invention in an amount of about 0.1% to about 10%, and preferably about 0.1% to about 5%, by weight, of the composition. To achieve the full advantage of the present invention, the antimicrobial agent is present in an amount of about 0.2% to about 5%, by weight, of the composition.

The antimicrobial compositions can be ready-to-use compositions, which typically contain 0.1% to about 7%, preferably 0.2% to about 5%, and most preferably about 0.2% to about 3%, of an antimicrobial agent, by weight of the composition. The antimicrobial compositions also can be formulated as concentrates that are diluted before use with one to about 100 parts water to provide an end-use composition. The concentrated compositions typically contain greater than about 0.1% and up to about 10%, by weight, of the antimicrobial agent. Applications also are envisioned wherein the end-use composition contains greater than 7%, by weight, of the antimicrobial agent.

The antimicrobial agents used in the present invention are aromatic carboxylic acids having a pKa of about 2.5 or greater, and preferably about 3 or greater. To achieve the full advantage of the present invention, the aromatic carboxylic acid has a pKa of about 3.5 or greater. Useful aromatic carboxylic acids have a structural formula

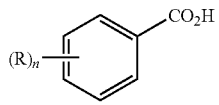

wherein R, independently, is selected from the group consisting of hydroxy, $C_{1-4}$alkyl, $C_{1-4}$alkoxy, amino, halo, phenyl, and benzyl; and n is 0, 1, or 2.

Specific examples of useful aromatic carboxylic acids include, but are not limited to, salicylic acid (i.e., o-hydroxybenzoic acid, pKa of about 3), benzoic acid (pKa of 4-0.19), o-aminobenzoic acid (pKa of 6.97), m-aminobenzoic acid (pKa of 4.78), p-amino-benzoic acid (pKa of 4.92), o-bromobenzoic acid (pK of 2.84), m-bromobenzoic acid (pKa of 3.86), o-chlorobenzoic acid (pKa of 2.92), m-chlorobenzoic acid (pKa of 3.82), p-chlorobenzoic acid (pKa of 3.98), 2,4-dihydroxybenzoic acid (pKa of 2.94), 2,5-dihydroxybenzoic acid (pKa of 2.97), 3,4-dihydroxybenzoic acid (pKa of 4.48), 3,5-dihydroxybenzoic acid (pKa of 4.04), ethylbenzoic acid (pKa of 4.35), m-hydroxybenzoic acid (pKa of 4.06), p-hydroxybenzoic acid (pKa of 4.48), o-iodobenzoic acid (pKa of 2.85), m-iodobenzoic acid (pKa of 3.80), methyl-o-aminobenzoic acid (pKa of 5.34), methyl-m-aminobenzoic acid (pKa of 5.10), methyl-o-aminobenzoic acid (pKa of 5.04), o-phenylbenzoic acid (pKa of 3.46), isopropylbenzoic acid (pKa of 4.48), and mixtures thereof. Preferred aromatic carboxylic acids are salicylic acid, benzoic acid, m-hydroxybenzoic acid, p-hydroxybenzoic, o-aminobenzoic acid, m-aminobenzoic acid, p-aminobenzoic acid, and mixtures thereof.

The composition is free of other standard antimicrobial agents, such as phenols, bisguanidine, trihalocarbanilides, quaternary ammonium chlorides, and the like.

Hydric Solvent

In addition to the aromatic carboxylic acid, a present composition also comprises a hydric solvent. The hydric solvent is present in an amount of about 5% to about 50%, and preferably about 7% to about 45%, by weight of the composition. To achieve the full advantage of the present invention, the composition contains about 10'-% to about 40% of a hydric solvent, by weight of the composition.

As defined herein, a "hydric solvent" is at least partially soluble in water, and is an organic compound containing one to six, and typically one to three, hydroxyl groups. A hydric solvent useful in the present invention has a Hansen solubility parameter of about 38 or less, and preferably about 35 or less. To achieve the full advantage of the present invention, the hydric solvent has a Hansen solubility parameter of about 30 or less, for example, down to 18. The Hansen solubility parameter is known to persons skilled in the art, and a discussion of the parameter can be found, for example, in the "CRC Handbook of Solubility Parameters and Other Cohesion Parameters, 2nd Edition," by Allan F. M. Barton, CRC Press, Boca Raton (1991).

Typically, the hydric solvent has a water solubility of at least 0.1 g of hydric solvent per 100 g of water at 25° C. There is no upper limit to the water solubility of the hydric solvent, e.g., the hydric solvent and water can be soluble in all proportions.

The term "hydric solvent," therefore, encompasses water-soluble alcohols, diols, triols, and polyols. Specific examples of hydric solvents include, but are not limited to, methanol, ethanol, isopropyl alcohol, n-butanol, n-propyl alcohol, ethylene glycol, propylene glycol, glycerol, diethylene glycol, dipropylene glycol, propylene glycol, tripropylene glycol, hexylene glycol, butylene glycol, 1,2,5-hexanetriol, sorbitol, PEG-4, benzyl alcohol, similar hydroxyl-containing compounds, and mixtures thereof.

pH-Adjusting Compound

In addition to the antimicrobial agent, and hydric solvent, a present antimicrobial composition contains a pH-adjusting compound in a sufficient amount to provide a composition pH of about 2 to about 5.5, preferably about 2 to about 5, and more preferably about 2.25 to about 5. The pH-adjusting compound typically is present in an amount of about 1% to about 5%, and preferably about 1% to about 4%, by weight, of the composition. To achieve the full advantage of the present invention, the pH-adjusting compound is present in an amount of about 1.5% to about 3.5%, by weight.

Examples of basic pH-adjusting compounds include, but are not limited to, ammonia; mono-, di-, and trialkyl amines; mono-, di-, and trialkanolamines; alkali metal and alkaline earth metal hydroxides; alkali metal phosphates; alkali sulfates; alkali metal carbonates; and mixtures thereof. However, the identity of the basic pH adjuster is not limited, and any basic pH-adjusting compound known in the art can be used. Specific, nonlimiting examples of basic pH-adjusting compounds are ammonia; sodium, potassium, and lithium hydroxide; sodium and potassium phosphates, including hydrogen and dihydrogen phosphates; sodium and potassium carbonate and bicarbonate; sodium and potassium sulfate and bisulfate; monoethanolamine; trimethylamine; isopropanolamine; diethanolamine; and triethanolamine.

The identity of an acidic pH-adjusting compound is not limited and any acidic pH-adjusting compound known in the art, alone or in combination, can be used. Examples of specific acidic pH-adjusting compounds are the mineral acids and polycarboxylic acids. Nonlimiting examples of mineral acids are hydrochloric acid, nitric acid, phosphoric acid, and sulfuric acid. Nonlimiting examples of polycarboxylic acids are citric acid, glycolic acid, and lactic acid.

Carrier

The carrier in the present composition comprises water.

Optional Ingredients

An antimicrobial composition of the present invention also can contain optional ingredients well known to persons skilled in the art. For example, the composition can contain a hydrotrope. The compositions also can contain other optional ingredients, such as dyes and fragrances, that are present in a sufficient amount to perform their intended function and do not adversely affect the antimicrobial efficacy of the composition. Such optional ingredients typically are present, individually, from 0% to about 5%, by weight, of the composition, and, collectively, from 0% to about 20%, by weight of the composition.

Classes of optional ingredients include, but are not limited to, dyes, fragrances, gelling agents, buffering agents, antioxidants, skin conditioners and protectants, chelating agents, opacifiers, vitamins, and similar classes of optional ingredients known to persons skilled in the art. Specific classes of optional ingredients include vitamins A, E, and C as vitamins; and EDTA compounds as chelating agents.

A present composition also can contain an optional hydrotrope. A hydrotrope is a compound that has the ability to enhance the water solubility of other compounds. A hydrotrope utilized in the present invention lacks surfactant properties, and typically is a short-chain alkyl aryl sulfonate. Specific examples of hydrotropes include, but are not limited to, sodium cumene sulfonate, ammonium cumene sulfonate, ammonium xylene sulfonate, potassium toluene sulfonate, sodium toluene sulfonate, sodium xylene-sulfonate, toluene sulfonic acid, and xylene sulfonic acid. Other useful hydrotropes include sodium polynaphthalene sulfonate, sodium polystyrene sulfonate, sodium methyl naphthalene sulfonate, and disodium succinate.

A present composition also can contain an optional gelling agent. If desired, the antimicrobial compositions contain a sufficient amount of gelling agent such that the composition is a viscous liquid, gel, or semisolid that can be easily applied to, and rubbed on, the skin. Persons skilled in the art are aware of the type and amount of gelling agent to include in the composition to provide the desired composition viscosity or consistency.

The term "gelling agent" as used here and hereafter refers to a compound capable of increasing the viscosity of a water-based composition, or capable of converting a water-based composition to a gel or semisolid. The gelling agent, therefore, can be organic in nature, for example, a natural gum or a synthetic polymer, or can be inorganic in nature.

As previously stated, the present compositions are free of a surfactant. A surfactant is not intentionally added to a present antibacterial composition, but may be present in an amount of 0% to about 0.2%, by weight, because a surfactant may be present in a commercial form of a gelling agent to help dispense the gelling agent in water. A surfactant also may be present as an additive or by-product in other composition ingredients. An extensive list of useful gelling agents is disclosed in U.S. Pat. No. 6,136,771, incorporated herein by reference.

Examples of optional skin conditioners include emollients, such as cetyl myristate, glyceryl dioleate, isopropyl myrisate, lanolin, methyl laurate. PPG-9 laurate, octyl palmitate, and PPG-5 lanoate, for example. The skin conditioner also can be a humectant, for example, glucamine and pyridoxine glycol. Occlusive skin conditioners, for example, aluminum lanolate, corn oil, methicone, coconut oil, stearyl stearate, phenyl trimethicone, trimyristin, olive oil, and synthetic wax, also can be used. Combinations of the classes of skin conditioners, in addition to miscellaneous skin conditioners known to persons skilled in the art, alone or in combination can be used. Non-limiting examples of miscellaneous skin conditioners also are disclosed in U.S. Pat. No. 6,136,771, incorporated herein by reference.

To demonstrate the new and unexpected results provided by the antimicrobial compositions of the present invention, the following Examples and Comparative Examples were prepared, and the ability of the compositions to control Gram positive and Gram negative bacteria, and viruses, was determined. The weight percent listed in each of the following examples represents the actual, or active, weight amount of each ingredient present in the composition. The compositions were prepared by blending the ingredients, as understood by those skilled in the art and as described below.

The following method was used in the testing of the examples:

Determination of Rapid Germicidal (Time Kill) Activity of Antimicrobial Products. The activity of antimicrobial compositions was measured by the time kill method, whereby the survival of challenged organisms exposed to an antibacterial test composition is determined as a function of time. In this test, a diluted aliquot of the composition is brought into contact with a known population of test bacteria for a specified time period at a specified temperature. The test composition is neutralized at the end of the time period, which arrests the antibacterial activity of the composition. The percent or, alternatively, log reduction from the original bacteria population is calculated. In general, the time kill method is known to those skilled in the art.

The composition can be tested at any concentration from 0% to 100%. The choice of which concentration to use is at the discretion of the investigator, and suitable concentrations are readily determined by those skilled in the art. For example, viscous samples usually are tested at 50% dilution, whereas nonviscous samples are not diluted. The test sample is placed in a sterile 250 ml beaker equipped with a magnetic stirring bar and the sample volume is brought to 100 ml, if needed, with sterile deionized water. All testing is performed in triplicate, the results are combined, and the average log reduction is reported.

The choice of contact time period also is at the discretion of the investigator. Any contact time period can be chosen. Typical contact times range from 15 seconds to 5 minutes, with 30 seconds and 1 minute being typical contact times. The contact temperature also can be any temperature, typically room temperature, or about 25 degrees Celsius.

The bacterial suspension, or test inoculum, is prepared by growing a bacterial culture on any appropriate solid media (e.g., agar). The bacterial population then is washed from the agar with sterile physiological saline and the population of the bacterial suspension is adjusted to about 108 colony forming units per ml (cfu/ml).

The table below lists the test bacterial cultures used in the following tests and includes the name of the bacteria, the ATCC (American Type Culture Collection) identification number, and the abbreviation for the name of the organism used hereafter.

| Organism Name | ATCC # | Abbreviation |
| --- | --- | --- |
| Staphylococcus aureus | 6538 | S. aureus |
| Escherichia coli | 11229 | E. coli |
| Klebsiella pneumoniae | 10031 | K. pneum. |
| Salmonella choleraesuis | 10708 | S. choler. |

S. aureus is a Gram positive bacteria, whereas E. coli, K. pneum, and S. choler. are Gram negative bacteria.

The beaker containing the test composition is placed in a water bath (if constant temperature is desired), or placed on a magnetic stirrer (if ambient laboratory temperature is desired). The sample then is inoculated with 1.0 ml of the test bacteria suspension. The inoculum is stirred with the test composition for the predetermined contact time. When the contact time expires, 1.0 ml of the test composition/bacteria mixture is transferred into 9.0 ml of Tryptone-Histidine-Tween Neutralizer Solution (THT). Decimal dilutions to a countable range then are made. The dilutions can differ for different organisms. Plate selected dilutions in triplicate on TSA+ plates (TSA+ is Trypticase Soy Agar with lecithin and polysorbate 80). The plates then are incubated for 25±2 hours, and the colonies are counted for the number of survivors and the calculation of percent or log reduction. The control count (numbers control) is determined by conducting the procedure as described above with the exception that THT is used in place of the test composition. The plate counts are converted to cfu/ml for the numbers control and samples, respectively, by standard microbiological methods.

The log reduction is calculated using the formula:

$$\text{Log reduction} = \log_{10}(\text{numbers control}) - \log_{10}(\text{test sample survivors}).$$

The following table correlates percent reduction in bacterial and viral populations to log reduction, and is referred to hereafter as the Antimicrobial Effectiveness Index (AEI):

| % Reduction | Log Reduction |
|---|---|
| 90 | 1 |
| 99 | 2 |
| 99.9 | 3 |
| 99.99 | 4 |
| 99.999 | 5 |

Compositions of the present invention have an AEI of at least 3, said AEI being equal to the $\log_{10}$ reduction at 30 seconds contact time determined by the time kill test as described above against a broad spectrum of bacterial species (i.e., a broad spectrum of bacterial species is defined as at least one Gram positive bacterial species and at least one Gram negative bacterial species).

The following examples illustrate the new and unexpected benefits provided by the compositions of the present invention. The AEI of each example was determined by testing against four different bacterial species, *S. aureus* is a Gram positive bacterial species, whereas the other three species are all Gram negative bacteria. The AEI of a composition of the present invention also was determined by testing against three different viral species, i.e., *Rhinovirus* 1A, *Rhinovirus* 2A, and *Rotavirus* Wa.

EXAMPLE 1

This example illustrates that compositions of the present invention exhibit excellent antimicrobial efficacy over a broad range of pH values. The compositions of this example were aqueous solutions containing, by weight, 3.3% salicylic acid, 11% ethanol, 27% dipropylene glycol, and sufficient sodium phosphate to provide the pH values indicated in the following table.

AEI Test results $\log_{10}$ Reduction at 30 seconds contact time

| pH | S. aureus | E. coli | K. pneum. | S. marcescens |
|---|---|---|---|---|
| 2.3 | >5.07 | >5.04 | >5.27 | >5.25 |
| 2.93 | >5.07 | >5.04 | >5.27 | >5.25 |
| 3.54 | 5.1 | >4.87 | >4.84 | >5.07 |
| 3.99 | >5.20 | >4.87 | >4.84 | >5.07 |
| 4.57 | >5.20 | >4.87 | >4.84 | >5.07 |
| 5.04 | >5.20 | >5.11 | >5.11 | >5.20 |
| 5.62 | 1.67 | >5.11 | >5.11 | >5.20 |
| 6.01 | 0.95 | >5.11 | >5.11 | >5.20 |

This example illustrates that compositions of the present invention, which utilize an aromatic carboxylic acid as the sole antimicrobial agent, maintain an AEI of at least 3 up to a pH of 5.04. This is an improvement over prior art compositions, which require either the presence of an additional antimicrobial agent or a pH of 3.5 or less.

EXAMPLE 2

Comparative

To demonstrate the effect of an aromatic carboxylic acid on the efficacy of the composition, several comparative compositions were prepared and tested at various pH levels, as summarized in the table below. The comparative compositions of this example were free of salicylic acid, and contained 11% ethanol, 27% dipropylene glycol, and sufficient phosphate buffer to provide the pH values indicated in the table.

AEI Test results $\log_{10}$ Reduction at 30 seconds contact time

| pH | S. aureus | E. coli | K. pneum. | S. marcescens |
|---|---|---|---|---|
| 2.35 | 1.81 | >5.04 | >5.27 | >5.25 |
| 2.87 | 0.97 | 0.56 | 1.01 | 0.63 |
| 3.80 | 0.75 | 0.15 | 0.81 | 0.0 |
| 5.38 | 0.0 | 0.0 | 0.51 | 0.0 |

Not one of the comparative formulations, which were free of an aromatic carboxylic acid present in an inventive composition, achieved an AEI of at least 3 at pH values between 2 and 5.5.

EXAMPLE 3

This example illustrates the effect of a hydric solvent on a composition of the present invention. Antibacterial effectiveness for various concentrations of salicylic acid in deionized water was determined over a range of pH values. The different pH values were achieved by using a proper amount of sodium phosphate. The table below summarizes the results of this test.

AEI Test Results $\log_{10}$ Reduction at 30 seconds contact time

| % SA | pH | S. aureus | E. coli | K. pneum. | S. marcescens |
|---|---|---|---|---|---|
| 0.0 | 4.56 | 0.0 | 0.3 | 0.0 | 0.2 |
| 0.0 | 2.99 | 0.84 | 0.88 | 1.7 | 0.76 |
| 0.2 | 4.02 | 0.0 | 0.0 | 0.06 | 0.0 |
| 0.2 | 3.51 | 0.0 | 0.0 | 0.1 | 0.0 |
| 0.2 | 3.02 | 0.0 | 0.38 | 0.67 | 0.17 |
| 3.3 | 4.58 | 0.56 | 0.66 | 0.0 | 0.67 |
| 3.3 | 5.58 | 0.0 | 0.0 | 0.0 | 0.0 |
| 3.3 | 6.59 | 0.0 | 0.35 | 0.0 | 0.53 |

SA = salicylic acid

These results illustrate the beneficial effect of including a hydric solvent in a present composition, i.e., salicylic acid alone did not provide an AEI of at least 3 at any tested pH.

EXAMPLE 4

This example illustrates the effect varying the amount of hydric solvent at a given pH and fixed concentration of salicylic acid. The compositions in this example all contained 2%, by weight, salicylic acid, the weight percent of dipropylene glycol (DPG) indicated in the table below, a sufficient amount of sodium phosphate to maintain a pH of 4, and deionized water.

| AEI Test results | | | | |
|---|---|---|---|---|
| | $Log_{10}$ Reduction at 30 seconds contact time | | | |
| % DPG | S. aureus | E. coli | K. pneum. | S. marcescens |
| 10 | 2.06 | 0.92 | >4.71 | 1.93 |
| 15 | 2.05 | 1.34 | >4.71 | 4.03 |
| 20 | 3.21 | 2.99 | >4.71 | >5.0 |
| 25 | 3.12 | 4.48 | >4.71 | >5.0 |
| 30 | 4.14 | >4.99 | >4.71 | >5.0 |
| 35 | >5.0 | 4.2 | >4.75 | >5.0 |

This example shows that an AEI of 3 is provided by compositions containing DPG concentrations at 20%, by weight, and higher. It is envisioned that a minimum amount of hydric solvent is needed in a composition to provide an AEI of at least 3, and this minimum amount is related to the identity of the hydric solvent, solution pH, and aromatic carboxylic acid concentration. The minimum amount of hydric solvent can be readily determined for any composition by the test criteria described in this example.

EXAMPLE 5

This example illustrates another composition of the present invention containing, by weight, 3.3% salicylic acid, 11% benzyl alcohol, 27% dipropylene glycol, and sufficient amount sodium phosphate to maintain a pH of 3.97. The composition was tested by the above-described time kill method and demonstrated an AEI of greater than 3.

EXAMPLE 6

This example illustrates another composition of the present invention containing, by weight, 3.3% salicylic acid, 22% isopropanol, and a sufficient amount of sodium phosphate to maintain a pH of 3.97. The composition was tested by the above-described time kill method and demonstrated an AEI of greater than 3.

EXAMPLE 7

This example demonstrates that aromatic carboxylic acids different from salicylic acid can be utilized in a composition of the present invention. The compositions of this example all contain, by weight, 3.3% benzoic acid, 11% ethanol, 27% dipropylene glycol, and a sufficient amount of sodium phosphate to maintain pH value listed for the different compositions, as indicated in the table below.

| AEI Test results | | | | |
|---|---|---|---|---|
| | $Log_{10}$ Reduction at 30 seconds contact time | | | |
| pH | S. aureus | E. coli | K. pneum. | S. marcescens |
| 2.93 | >5.0 | >4.71 | >4.87 | >5.04 |
| 3.95 | >5.0 | >4.71 | >4.87 | >5.04 |
| 5.00 | >5.0 | >4.71 | >4.87 | >5.04 |

These compositions of the present invention each demonstrated an AEI of at least 3 over a wide range of pH values. A comparative composition, absent an aromatic carboxylic acid, failed to demonstrate an AEI of 3 at a pH of 3.02.

EXAMPLE 8

Comparative

This example demonstrates that aliphatic carboxylic acids do not perform as effective antimicrobial agents. Thus, a composition containing, by weight, 0.2% cyclohexanecarboxylic acid, 11% ethanol, and 27% dipropylene glycol was prepared. The pH of the solution was maintained at 4, and the composition was tested to determine the AEI. The composition did not demonstrate an AEI of at least 3.

EXAMPLE 9

A composition of the invention (i.e., the "active" composition) was prepared by admixing 2% salicylic acid by weight, 25% dipropylene glycol by weight, water, and sufficient sodium phosphate to provide a pH of about 3.7. Additionally, an identical "placebo" composition was prepared absent salicylic acid. The active and the placebo compositions both were tested against Rhinovirus 1A (ATCC VR1364), Rhinovirus 2A (ATCC VR382), and Rotavirus Wa (Sera type 1, clinical isolate) for antiviral efficacy (i.e., the ability to inactivate virus) in suspension. The test was conducted in accordance with ASTM Test Method E1052-96 ("Standard test method for efficacy of antimicrobial agents against viruses in suspension"), with modification as to virus type and contact time, as is obvious to those skilled in the art of antiviral efficacy testing. The antiviral efficacy of this test is reported as log reductions of virus particles at the tested contact times. The following table summarizes the efficacy test results ($log_{10}$ reductions) for the active and placebo compositions at the various contact times (in seconds).

| | $Log_{10}$ Reductions at 30, 60, and 300 seconds | | | | | | | |
|---|---|---|---|---|---|---|---|---|
| | Rhinovirus 1A | | | Rhinovirus 2A | | | Rotavirus Wa | | |
| Sample | 30 | 60 | 300 | 30 | 60 | 300 | 30 | 60 | 300 |
| Placebo | 0.4 | 0.1 | 0.2 | 0.3 | 0.3 | 0.4 | >0.2 | 0.2 | >0.4 |
| Active | 4.4 | 4.5 | 4.7 | 3.5 | 3.3 | 3.7 | >4.8 | 4.2 | 4.6 |

Example 9 clearly shows that a present composition containing salicylic acid is highly effective at reducing viral populations, as demonstrated by the high log reductions of the active composition versus the three tested viruses compared to the placebo composition. The reduction of viral populations is important in the art of antimicrobial compositions because Rhinovirus causes common colds and Rotavirus causes gastrointestinal diseases.

The antimicrobial compositions of the present invention have several practical end uses, including hand cleansers, mouthwashes, surgical scrubs, body splashes, hand sanitizers, and similar personal care products, such as skin conditioners. Additional types of compositions include foamed compositions, such as creams, mousses, and the like, and compositions containing organic and inorganic filler materials, such as emulsions, lotions, creams, pastes, and the like. The compositions further can be used as an antimicrobial cleanser for hard surfaces, for example, sinks and countertops in hospitals, food service areas, and meat processing plants. The present antimicrobial compositions can be manufactured as dilute ready-to-use compositions, or as concentrates that are diluted prior to use.

The compositions also can be incorporated into a web material to provide an antimicrobial wiping article. The wiping article can be used to clean and sanitize skin or inanimate surfaces.

The present antimicrobial compositions provide the advantages of a broad spectrum skill of Gram positive and Gram negative bacteria, and viruses, in short contact times. The short contact time for a substantial log reduction of bacteria, and viruses, is important in view of the typical 15 to 60 second time frame used to cleanse and sanitize the skin and inanimate surfaces.

Obviously, many modifications and variations of the invention as hereinbefore set forth can be made without departing from the spirit and scope thereof, and, therefore only such limitations should be imposed as are indicated by the appended claims.

What is claimed is:

1. A method of reducing a bacteria population on a surface comprising contacting the surface with an antimicrobial composition for 30 seconds to achieve a log reduction of at least 3 against *S. aureus* or a log reduction of at least 3 against *E. coli*, wherein the antimicrobial composition comprises:
   (a) about 0.1% to about 10%, by weight, of an aromatic carboxylic acid, wherein the aromatic carboxylic acid has a structure

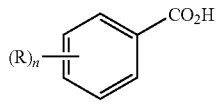

wherein R, independently, is selected from the group consisting of hydroxy, $C_{1-4}$alkyl, $C_{1-4}$alkoxy, amino, halo, phenyl, and benzyl; and n is 1 or 2;
   (b) about 10% to about 40%, by weight, of a hydric solvent comprising dipropylene glycol;
   (c) a sufficient amount of a pH-adjusting compound to provide a pH of about 2 to about 5.5; and
   (d) a carrier comprising water,
   wherein the aromatic carboxylic acid is the sole antimicrobial agent in the composition,
   and the composition contains 0% to 0.2%, by weight, of a surfactant.

2. The method of claim 1 comprising about 0.1% to about 5%, by weight, of the aromatic carboxylic acid.

3. The method of claim 1 wherein the aromatic carboxylic acid has a pKa of about 2.5 to about 7.

4. The method of claim 1 wherein the aromatic carboxylic acid is selected from the group consisting of salicylic acid, o-aminobenzoic acid, m-aminobenzoic acid, p-aminobenzoic acid, o-bromobenzoic acid, m-bromobenzoic acid, o-chlorobenzoic acid, m-chlorobenzoic acid, p-chlorobenzoic acid, 2,4-dihydroxybenzoic acid, 2,5-dihydroxybenzoic acid, 3,4-dihydroxybenzoic acid, 3,5-dihydroxybenzoic acid, ethylbenzoic acid, m-hydroxybenzoic acid, p-hydroxybenzoic acid, o-iodobenzoic acid, m-iodobenzoic acid, methyl-o-aminobenzoic acid, methyl-m-aminobenzoic acid, methyl-o-aminobenzoic acid, o-phenylbenzoic acid, isopropylbenzoic acid, and mixtures thereof.

5. The method of claim 1 wherein the antimicrobial agent comprises salicylic acid, m-hydroxybenzoic acid, p-hydroxybenzoic, o-aminobenzoic acid, m-aminobenzoic acid, p-aminobenzoic acid, or a mixture thereof.

6. The method of claim 1 wherein the hydric solvent consists of about 20% to about 35%, by weight, dipropylene glycol.

7. The method of claim 1 wherein the composition further comprises additional solvents selected from the group consisting of methanol, ethanol, isopropyl alcohol, n-butanol, n-propyl alcohol, ethylene glycol, propylene glycol, glycerol, diethylene glycol, tripropylene glycol, hexylene glycol, butylene glycol, 1,2,5-hexanetriol, sorbitol, PEG-4, and mixtures thereof.

8. The method of claim 1 wherein the composition further comprises additional solvents selected from isopropanol, ethanol, and a mixture thereof.

9. The method of claim 1 wherein the pH-adjusting compound is present in an amount of about 1% to about 5%, by weight, of the composition.

10. The method of claim 1 having a pH of about 2 to about 5.

11. The method of claim 1 wherein the pH-adjusting compound comprises sodium phosphate, sodium dihydrogen phosphate, disodium hydrogen phosphate, sodium hydroxide, potassium hydroxide, or a mixture thereof.

12. The method of claim 1 comprising:
   (a) about 0.2% to about 5%, by weight, of the aromatic carboxylic acid as the sole antimicrobial agent;
   (b) about 10% to about 40%, by weight, of dipropylene glycol;
   (c) a sufficient amount of the pH-adjusting compound to provide a pH of about 2.25 to about 5.

13. The method of claim 1 wherein the composition achieves a log reduction of at least 3 against *S. aureus* and a log reduction of at least 3 against *E. coli*.

14. The method of claim 1 wherein a log reduction of at least 3 is achieved in a viral population.

15. The method of claim 14 wherein the viral population comprises Rhinovirus 1A, Rhinovirus 2A, Rotavirus Wa, and mixtures thereof.

16. The method of claim 1 wherein the surface is a skin of a mammal.

17. A method of reducing a viral population on a surface comprising contacting the surface with a composition of for 30 seconds to achieve a viral log reduction of at least 3, wherein the composition comprises:
   (a) about 0.1% to about boo, by weight, of an aromatic carboxylic acid, wherein the aromatic carboxylic acid has a structure

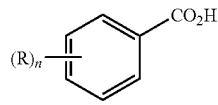

wherein R, independently, is selected from the group consisting of hydroxy, $C_{1-4}$alkyl, $C_{1-4}$alkoxy, amino, halo, phenyl, and benzyl; and n is 1 or 2;
   (b) about 10% to about 40%, by weight, of a hydric solvent comprising dipropylene glycol;
   (c) a sufficient amount of a pH-adjusting compound to provide a pH of about 2 to about 5.5; and
   (d) a carrier comprising water,
   wherein the aromatic carboxylic acid is the sole antimicrobial agent in the composition, and the composition contains 0% to 0.2%, by weight, of a surfactant.

18. The method of claim 17 wherein the viral population comprises Rhinovirus 1A, Rihinovirus 2A, Rotavirus Wa, and mixtures thereof.

19. The method of claim 17 wherein the surface is a skin of a mammal.

20. The method of claim 12 wherein the antimicrobial carboxylic acid comprises salicyclic acid.

21. The method of claim 12 wherein the composition further comprises additional solvents selected from ethanol, isopropanol, and mixtures thereof.

* * * * *

UNITED STATES PATENT AND TRADEMARK OFFICE
CERTIFICATE OF CORRECTION

PATENT NO.         : 7,592,300 B2                              Page 1 of 1
APPLICATION NO.    : 10/720862
DATED              : September 22, 2009
INVENTOR(S)        : Timothy J. Taylor et al.

It is certified that error appears in the above-identified patent and that said Letters Patent is hereby corrected as shown below:

At Column 14, line 46 claim 17, "boo" should be -- 10% --.

Signed and Sealed this

Twenty-fifth Day of May, 2010

David J. Kappos
*Director of the United States Patent and Trademark Office*